US007431920B2

(12) United States Patent
Liu et al.

(10) Patent No.: US 7,431,920 B2
(45) Date of Patent: Oct. 7, 2008

(54) METHOD OF TREATING IL-10 DEFICIENCY

(75) Inventors: Chih-Ping Liu, San Francisco, CA (US); Lorelie H. Villarete, Alameda, CA (US); Stephen N. Kirnon, San Ramon, CA (US)

(73) Assignee: Pepgen Corporation, Los Angeles, CA (US)

( * ) Notice: Subject to any disclaimer, the term of this patent is extended or adjusted under 35 U.S.C. 154(b) by 91 days.

(21) Appl. No.: 11/112,369

(22) Filed: Apr. 22, 2005

(65) Prior Publication Data
US 2005/0265968 A1 Dec. 1, 2005

Related U.S. Application Data

(63) Continuation-in-part of application No. 11/078,608, filed on Mar. 10, 2005, now abandoned, and a continuation-in-part of application No. 11/040,706, filed on Jan. 21, 2005, and a continuation-in-part of application No. 10/884,741, filed on Jul. 2, 2004, now abandoned, and a continuation-in-part of application No. 10/825,457, filed on Apr. 14, 2004, now abandoned, and a continuation-in-part of application No. 10/825,382, filed on Apr. 14, 2004, and a continuation-in-part of application No. 10/825,068, filed on Apr. 14, 2004, and a continuation-in-part of application No. 10/824,710, filed on Apr. 14, 2004, now Pat. No. 7,083,782.

(60) Provisional application No. 60/552,279, filed on Mar. 10, 2004.

(51) Int. Cl.
*A61K 38/21* (2006.01)

(52) U.S. Cl. .................. 424/85.4; 424/85.7; 424/85.2

(58) Field of Classification Search ........................ None
See application file for complete search history.

(56) References Cited

U.S. PATENT DOCUMENTS

| | | | |
|---|---|---|---|
| H22 H | 2/1986 | Creasey et al. | |
| 4,683,195 A | 7/1987 | Mullis et al. | |
| 4,683,202 A | 7/1987 | Mullis | |
| 4,752,479 A | 6/1988 | Briggs et al. | |
| 4,766,068 A | 8/1988 | Oeda et al. | |
| 4,769,238 A | 9/1988 | Rutter et al. | |
| 4,822,605 A | 4/1989 | Powell | |
| 5,098,702 A | 3/1992 | Zimmerman et al. | |
| 5,128,126 A | 7/1992 | Boniver | |
| 5,368,854 A | 11/1994 | Rennick | |
| 5,376,368 A | 12/1994 | Ulich | |
| 5,425,940 A | 6/1995 | Zimmerman et al. | |
| 5,563,126 A | 10/1996 | Allen et al. | |
| 5,632,983 A | 5/1997 | Hadden | |
| 5,705,363 A | 1/1998 | Imakawa | |
| 5,880,114 A | 3/1999 | Deluca et al. | |
| 5,906,816 A | 5/1999 | Soos et al. | |
| 5,942,223 A | 8/1999 | Bazer et al. | |
| 5,958,402 A | 9/1999 | Bazer et al. | |
| 6,036,949 A | 3/2000 | Richards et al. | |
| 6,060,450 A | 5/2000 | Soos et al. | |
| 6,080,742 A | 6/2000 | Germann et al. | |
| 6,083,919 A | 7/2000 | Johnson et al. | |
| 6,346,243 B1 | 2/2002 | Brod | |
| 6,372,206 B1 | 4/2002 | Soos et al. | |
| 6,403,562 B1 | 6/2002 | Johnson et al. | |
| 6,528,496 B1 | 3/2003 | Allen et al. | |
| 6,613,354 B2 | 9/2003 | Depui et al. | |
| 6,699,496 B1 | 3/2004 | Kojima et al. | |
| 6,942,854 B2 | 9/2005 | Soos et al. | |
| 7,083,782 B2 | 8/2006 | Liu et al. | |
| 2002/0013452 A1 | 1/2002 | Johnson et al. | |
| 2003/0012766 A1 | 1/2003 | Soos et al. | |
| 2003/0017136 A1 | 1/2003 | Cruz et al. | |
| 2003/0049277 A1 | 3/2003 | Sokawa et al. | |
| 2003/0055013 A1 | 3/2003 | Brass | |
| 2003/0086901 A1 | 5/2003 | Cruz et al. | |
| 2003/0130486 A1 | 7/2003 | Villarete et al. | |
| 2003/0185799 A1 | 10/2003 | Rudolph | |
| 2003/0219405 A1 | 11/2003 | Sokawa et al. | |
| 2003/0229044 A1 | 12/2003 | Steinman et al. | |

(Continued)

FOREIGN PATENT DOCUMENTS

EP 0 814 831 1/1998

(Continued)

OTHER PUBLICATIONS

Petereit et al., Low interleukin-10 production is associated with higher disability and MRI lesion load in secondary progressive multiple sclerosis, 2003, Journal of the neurological sciences, vol. 206, pp. 209-214.*

(Continued)

*Primary Examiner*—David Romeo
*Assistant Examiner*—Ian Dang
(74) *Attorney, Agent, or Firm*—Judy M. Mohr; King & Spalding LLP

(57) ABSTRACT

A method for treating an IL-10 deficiency in a human subject is described, where a person having an IL-10 deficiency is identified and treated with interferon-tau (IFNτ) at a dose sufficient to increase the IL-10 level.

9 Claims, 3 Drawing Sheets

U.S. PATENT DOCUMENTS

| | | |
|---|---|---|
| 2003/0232033 A1 | 12/2003 | Cantrell |
| 2004/0009896 A1 | 1/2004 | Glynn et al. |
| 2004/0013643 A1 | 1/2004 | Mach |
| 2004/0013695 A1 | 1/2004 | Vande-Velde |
| 2004/0086508 A1 | 5/2004 | Skurkovich et al. |
| 2004/0247565 A1 | 12/2004 | Liu et al. |
| 2005/0014734 A1 | 1/2005 | Chang |
| 2005/0265968 A1 | 12/2005 | Liu et al. |

FOREIGN PATENT DOCUMENTS

| | | |
|---|---|---|
| EP | 1 114 998 A2 | 7/2001 |
| EP | 1 241 242 A2 | 9/2002 |
| WO | WO 90/09806 | 9/1990 |
| WO | WO 94/10313 | 5/1994 |
| WO | WO 96/28183 | 9/1996 |
| WO | WO 97/33607 | 9/1997 |
| WO | WO 02/06343 A2 | 1/2002 |
| WO | WO 03/061728 A2 | 7/2003 |
| WO | WO2005/087254 A2 | 9/2005 |

OTHER PUBLICATIONS

Abou Taleb et al., *The Journal of the Egyptian National Cancer*, 12(1):59-64 (2000).
Alexenko et al., *J. Interferon Cytokine Res.*, 19:1335-1341 (1999).
Heeschen et al., Circulation, 107:2109-2114 (2003).
Van Roon et al., *The Journal of Rheumatology* 30(4):648-651 (2003).
Hugh McDevitt, "Specific Antigen Vaccination to Treat Autoimmune Disease" PNAS, 101(Suppl 2) 14627-14630 (2004).
White D., Fenner FJ "Medical Virology" Fourth Edition, Academic Press: New York, 1994.
Alexenko, A.P., et al., *Journal of Interferon and Cytokine Research* 17:769-779, (1997).
Bagaeva, L.V., et al., *Journal of Neuroimmunology* 137:109-116, (2003).
van Boxel-Dexaire, A.H.H., et al., *Ann Neurol* 45:695-703, (1999).
Brennan, F.R., et al., *J Med Microbiol* 41:20-28, (1994).
Brod, S.A., et al., *Journal of Neuroimmunology* 58:61-69, (1995).
Brod, S.A., et al., *Diabetologia* 41:1227-1232, (1998).
Brod, S.A., *Journal of Interferon and Cytokine Research* 19:841-852, (1999).
Carter, C.R.D., et al., *Clin Exp Immunol* 135:233-239, (2004).
Chaouat, G., et al., *J Immunology* 154(9):4261-4268, (1995).
Elices, M.J., *Current Opinion in Investigational Drugs* 4(11):1354-1362, (2003).
Filion, L.G., et al., *Clin Immunol* 106:127-138, (2003).
Groetzner, J., et al., *Transplantation* 77(4):568-574, (2004).
Kappos, L., et al., *J Neurol*, 251(Suppl 5):V/57-V/64, (2004).
Khan, O.A., et al., *Mult Scler* 4(2):63-69, (1998).
Killestein, J. and Polman, C.H., *Curr Opin Neurol*, 18:253-260, (2005).
Li, M.C. and He, S.H., *World Journal of Gastroenterology* 10:620-625, (2004).
Losy, J., et al., *Folia Neuropathol* 40(4):173-175, (2002).
Makhlouf, K., et al., *Journal of Neuroimmunology* 119:145-149, (2001).
Martin, J., et al., *Cytokine* 10(8):635-644, (1998).
Miller, D.H., et al., *N Engl J Med* 348:15-23, (2003).
Moldovan, I.R., et al., *Journal of Neuroimmunology* 141:132-140, (2003).
Mujtaba, M.G., et al., *J Neurol* 75(1-2):35-42, (1997).
Mujtaba, M.G., et al., *Cell Immunol* 186(2):94-102, (1998).
Nakajima, A., and Yoshihiro, S., *Journal of Interferon and Cytokine Research* 22:397-402, (2002).
Olek, M.J., et al., *Neurology* 56(Suppl 3):A76, (2001).
Petereit, H.F., et al., *Journal of Neurological Sciences* 206:209-214, (2003).
Pontzer, C.H., et al., *Biochemical and Biophysical Research Communications* 152(2):801-807, (1988).
Pontzer, C.H., *Cancer Research* 51:5304-5307, (1991).
van Roon, J., et al., *Journal of Rheumatology* 30:648-651, abstract only.
Sandborn, W.J. and Yednock, T.A., *American Journal of Gastroenterology* 98(11):2372-2382, (2003).
Soos, J.M., et al., *Journal of Interferon and Cytokine Research* 15:39-45, (1995).
Tuo, W., et al., *J Interferon and Cytokine Research* 19(2):179-187, (1999).
Tuohy, V.K., et al., *Journal of Neuroimmunology* 111:55-63, (2000).
Vanderhoff, B.T., and Tahboub, R.M., *Am Fam Physician* 66:273-280, (2002).
Asadullah, K., et al., *Pharmacol Rev* 55(2):241-269, (2003).
Fainardi, E., et al., *J of Neuroimmunology* 142:149-158, (2003).
Goldman, M. and Velu, T., *Advances in Nephrology* 24:79-90, (1995).
Jacobs, R., et al., *Rheumatology* 40:868-875, (2001).
Kozlowski, L., et al., *Annales Academiae Medicae Bialostocensis* 48:82-84, (2003).
Leon, L.R., et al., *Annals of the New York Academy of Sciences* 856:69-75, (1998).
Macdougall, I.C. and Cooper, A.C., *Nephrol Dial Transplant* 17(Supp 11):39-43, (2002).
Murray, H.W., et al., *Infection and Immunity* 70(11):6284-6293, (2002).
Rennick, D.M. and Fort, M.M., *Am J Physiol Gastrointest Liver Physiol* 278:G829-G833, (2000).
Soltys, J., et al., *J of Immunol* 168:1903-1910, (2002).
Soos, J.M., et al., *J Immunol* 169(5):2231-2235, (2002).
Soos, J.M., et al., *J of Neuroimmunology* 75:43-50, (1997).
Wang, B., et al., *J Immunol* 162:277-283, (1999).
Waubant, E., et al., *J of Neuroimmunology* 112:139-145, (2001).

* cited by examiner

SEQUENCE LISTING

<160> NUMBER OF SEQ ID NOS: 2

<210> SEQ ID NO 1
<211> LENGTH: 172
<212> TYPE: PRT
<213> ORGANISM: Ovis aries

<400> SEQUENCE: 1

```
Cys Tyr Leu Ser Arg Lys Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
65                  70                  75                  80

Leu Leu Glu Gln Leu Cys Thr Gly Leu Gln Gln Gln Leu Asp His Leu
                85                  90                  95

Asp Thr Cys Arg Gly Gln Val Met Gly Glu Glu Asp Ser Glu Leu Gly
            100                 105                 110

Asn Met Asp Pro Ile Val Thr Val Lys Lys Tyr Phe Gln Gly Ile Tyr
        115                 120                 125

Asp Tyr Leu Gln Glu Lys Gly Tyr Ser Asp Cys Ala Trp Glu Ile Val
    130                 135                 140

Arg Val Glu Met Met Arg Ala Leu Thr Val Ser Thr Thr Leu Gln Lys
145                 150                 155                 160

Arg Leu Thr Lys Met Gly Gly Asp Leu Asn Ser Pro
                165                 170
```

<210> SEQ ID NO 2
<211> LENGTH: 172
<212> TYPE: PRT
<213> ORGANISM: Artificial
<220> FEATURE:
<223> OTHER INFORMATION: Recombinant IFNTau Based on Ovis aries Sequence

<400> SEQUENCE: 2

```
Cys Tyr Leu Ser Glu Arg Leu Met Leu Asp Ala Arg Glu Asn Leu Lys
1               5                   10                  15

Leu Leu Asp Arg Met Asn Arg Leu Ser Pro His Ser Cys Leu Gln Asp
            20                  25                  30

Arg Lys Asp Phe Gly Leu Pro Gln Glu Met Val Glu Gly Asp Gln Leu
        35                  40                  45

Gln Lys Asp Gln Ala Phe Pro Val Leu Tyr Glu Met Leu Gln Gln Ser
    50                  55                  60

Phe Asn Leu Phe Tyr Thr Glu His Ser Ser Ala Ala Trp Asp Thr Thr
```

-continued

```
            65                  70                  75                  80
Leu Leu Glu Gln Leu Cys Thr Gly Leu Gln Gln Gln Leu Asp His Leu
                85                      90                      95

Asp Thr Cys Arg Gly Gln Val Met Gly Glu Glu Asp Ser Glu Leu Gly
               100                     105                     110

Asn Met Asp Pro Ile Val Thr Val Lys Lys Tyr Phe Gln Gly Ile Tyr
               115                     120                     125

Asp Tyr Leu Gln Glu Lys Gly Tyr Ser Asp Cys Ala Trp Glu Ile Val
           130                     135                     140

Arg Val Glu Met Met Arg Ala Leu Thr Val Ser Thr Thr Leu Gln Lys
145                     150                     155                     160

Arg Leu Thr Lys Met Gly Gly Asp Leu Asn Ser Pro
               165                     170
```

METHOD OF TREATING IL-10 DEFICIENCY

CROSS REFERENCE TO RELATED APPLICATIONS

This application is a continuation-in-part of U.S. patent application Ser. Nos. 11/078,608, filed Mar. 10, 2005, now abandoned; 11/040,706 filed Jan. 21, 2005, 10/884,741, filed Jul. 2, 2004, now abandoned; 10/825,457 filed Apr. 14, 2004, now abandoned; 10/825,382 filed Apr. 14, 2004, pending; 10/825,068 filed Apr. 14, 2004, pending; and 10/824,710, filed Apr. 14, 2004, now U.S. Patent No. 7,083,782, all of which claim the benefit of U.S. Provisional Patent Application Ser. No. 60/552,279 filed Mar. 10, 2004. These applications are expressly incorporated by reference herein in their entirety.

FIELD OF THE INVENTION

The present invention relates to a method of treating IL-10 deficiency in a human subject.

BACKGROUND OF THE INVENTION

The human immune system has a multitude of natural and adaptive immune mechanisms and reactions for maintaining a healthy state. Immune responses are often divided into humoral and cell-mediated response. Humoral immunity refers broadly to antibody production and actions by B-cells including plasma cells. Cellular immunity is mediated by cells including T-cells, monocytes, macrophages, and histiocytes. T-cells and B-cells are two broad categories of lymphocytes, and T-cells are further categorized according to their various functions or markers, for example as, T-helper (Th) cells or T-suppressor cells. T-helper cells can be divided into different subsets that are distinguished by their cytokine production profiles. Th1 T cell clones produce interleukin-2 (IL-2) and interferon-gamma (IFN-γ), whereas Th2 cell clones secrete IL-10, IL-4, and IL-5. Both classes of Th cell clones produce cytokines such as tumor necrosis factor-alpha (TNF-α), IL-3, and granulocyte-macrophage colony stimulating factor (GM-CSF). A third category of Th cells (Th0) produces IL-2, IFN-γ, IL-4, IL-5, TNF-α, IL-3, and GM-CSF simultaneously.

The different cytokine production patterns of Th1 and Th2 cells reflect their helper functions. Th1 cells are predominantly involved in delayed-type hypersensitivity (DTH) responses, whereas Th2 cells are associated with antibody production. Since antibody (Th2 pathways) and DTH (Th1 pathways) responses are often mutually exclusive, Th1 and Th2 cells are thought to have cross-regulatory effects. IFN-γ produced by Th1 cells inhibits proliferation of Th2 cells, and IL-10 produced by Th2 cells inhibits cytokine synthesis by Th1 cell clones, especially IFN-γ and IL-2 production.

IL-10 is a pluirpotent cytokine with potent effects on various cell populations, in particular circulating and resident immune cells, and thus has broad effects in immunoregulation and host defense. Agents capable of stimulating endogenous production of IL-10 in order to mediate the immune response would be advantageous for therapy of various diseases and conditions.

SUMMARY OF THE INVENTION

In one aspect, the invention includes a treatment method comprising identifying a human subject having or likely to have an IL-10 deficiency and administering interferon-tau in an amount effective to increase blood IL-10 level relative to the blood IL-10 level before administering interferon-tau.

In one embodiment, the subject suspected of having an IL-10 deficiency is identified by obtaining a blood sample from the subject and analyzing the sample for IL-10 concentration. In another embodiment, the subject suspected of having an IL-10 deficiency is identified by a diagnosis of a condition typically characterized by a decreased IL-10 blood level.

In another embodiment, the subject identified as having an IL-10 deficiency is asymptomatic, other than a decreased IL-10 blood level.

In another embodiment, the subject is treated with interferon-tau at a first dose for a first period of time, and then the blood IL-10 concentration is determined after the first period of time has lapsed, and a second dose of interferon-tau is administered for a second period of time. In one embodiment, the second dose is less than the first dose. In another embodiment, the second dose is greater than the first dose. In still another embodiment, the first period of time is shorter than the second period of time. Typically, and in another embodiment, the first period of time is about one month or less.

In another embodiment, interferon-tau is administered to a subject who is at risk of developing a condition that is caused, at least in part, by an IL-10 deficiency.

In another embodiment, interferon-tau is administered to a subject suffering from a condition that is, or which has symptoms that are, exacerbated by an IL-10 deficiency.

In exemplary embodiments, conditions and/or symptoms that are exacerbated by decreased blood IL-10 levels include autoimmune condition, viral infections, and conditions characterized by inflammation.

In another embodiment, the subject having or likely to have an IL-10 deficiency is identified by physical symptoms associated with an existing autoimmune condition.

In another embodiment, the subject having or likely to have an IL-10 deficiency is identified by physical symptoms associated with a viral infection.

In another embodiment, the subject having or likely to have an IL-10 deficiency is identified by physical symptoms associated with a condition characterized by inflammation.

In yet another embodiment, the interferon-tau is administered orally to the subject. In still another embodiment, the dose is greater than $5 \times 10^8$ Units per day, more preferably the dose is greater than $1 \times 10^9$ Units per day.

In another embodiment, the method includes monitoring the IL-10 level of the subject, after administration of IFNτ for an initial period of time, to ascertain whether the IL-10 level is increased as a result of initial administration of IFNτ. Such monitoring can be achieved by obtaining a blood sample from the subject and analyzing the sample for IL-10 concentration.

These and other objects and features of the invention will be more fully appreciated when the following detailed description of the invention is read in conjunction with the accompanying drawings.

BRIEF DESCRIPTION OF THE SEQUENCES

Figure 1:
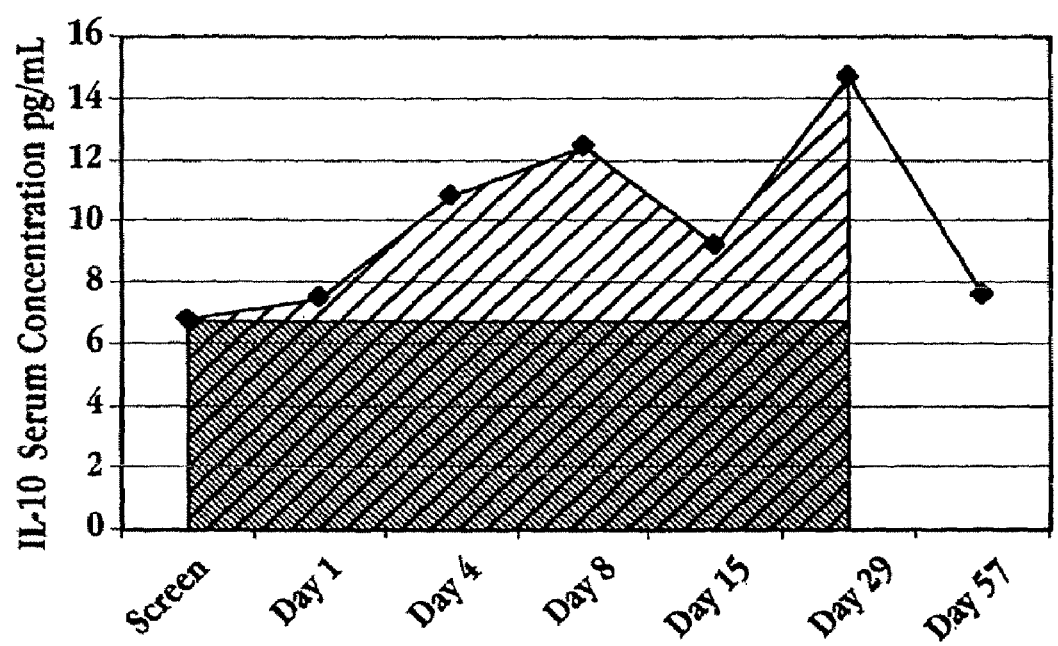
FIG. 1 is a plot of serum IL-10 concentration, in pg/mL, as a function of time during a 28 day treatment period of a subject with IFNτ.

SEQ ID NO:1 corresponds to an amino acid sequence of mature ovine interferon-1 (IFNτ; oTP-1; GenBank Accession No. Y00287; PID g1358).

SEQ ID NO:2 corresponds to an amino acid sequence of mature ovine IFNτ, where the amino acid residues at positions 5 and 6 of the sequence are modified relative to the sequence of SEQ ID NO:1.

DETAILED DESCRIPTION OF THE INVENTION

I. Definitions

Interferon-tau, abbreviated as IFNτ or interferon-τ, refers to any one of a family of interferon proteins having at least one characteristic from each of the following two groups of characteristics: (i) (a) anti-luteolytic properties, (b) anti-viral properties, (c) anti-cellular proliferation properties; and (ii) about 45 to 68% amino acid homology with α-interferons and greater than 70% amino acid homology to known IFNτ sequences (e.g., Ott, et al., *J. Interferon Res.*, 11:357 (1991); Helmer, et al., *J. Reprod. Fert.*, 79:83 (1987); Imakawa, et al., *Mol. Endocrinol*, 3:127 (1989); Whaley, et al., *J. Biol. Chem.*, 269:10846 (1994); Bazer, et al., WO 94/10313 (1994)). Amino acid homology can be determined using, for example, the LALIGN program with default parameters. This program is found in the FASTA version 1.7 suite of sequence comparison programs (Pearson and Lipman, *PNAS*, 85:2444 (1988); Pearson, *Methods in Enzymology*, 183:63 (1990); program available from William R. Pearson, Department of Biological Chemistry, Box 440, Jordan Hall, Charlottesville, Va.). IFNτ sequences have been identified in various ruminant species, including but not limited to, cow (Bovine sp., Helmer, S. D., *J. Reprod. Fert.*, 79:83 (1987); Imakawa, K., *Mol. Endocrinol.*, 119:532 (1988)), sheep (*Ovine* sp.), musk ox (*Ovibos* sp.), giraffe (*Giraffa* sp., GenBank Accession no. U55050), horse (*Equus caballus*), zebra (*Equus burchelli*, GenBank Accession no. NC005027), hippopotamus (*Hippopotamus* sp.), elephant (*Loxodonta* sp.), llama (*Llama glama*), goat (*Capra* sp., GenBank Accession nos. AY357336, AY357335, AY347334, AY357333, AY357332, AY357331, AY357330, AY357329, AY357328, AY357327), and deer (*Cervidae* sp.). The nucleotide sequences of IFNτ for many of these species are reported in public databases and/or in the literature (see, for example, Roberts, R. M. et al., *J. Interferon and Cytokine Res.*, 18:805 (1998), Leaman D. W. et al., *J. Interferon Res.*, 12:1 (1993), Ryan, A. M. et al., *Anim. Genet.*, 34:9 (1996)). The term "interferon-tau" intends to encompass the interferon-tau protein from any ruminant species, exemplified by those recited above, that has at least one characteristic from each of the two groups of characteristics listed above.

*Ovine* IFNτ (OvIFNτ) refers to a protein having the amino acid sequence as identified herein as SEQ ID NO:1, and to proteins having amino acid substitutions and alterations such as neutral amino acid substitutions that do not significantly affect the activity of the protein, such as the IFNτ protein identified herein as SEQ ID NO:2. More generally, an ovine IFNτ protein is one having about 80%, more preferably 90%, sequence homology to the sequence identified as SEQ ID NO:1. Sequence homology is determined, for example, by a strict amino acid comparison or using one of the many programs commercially available.

Treating a condition refers to administering a therapeutic substance effective to reduce the symptoms of the condition and/or lessen the severity of the condition.

II. Treatment Methods

In one aspect, the invention relates to a method of treating an IL-10 deficiency in a human subject. A subject having or likely to have a decreased IL-10 level is identified, by one of several approaches described below. Interferon-tau (IFNτ) is administered to the subject in an amount effective to increase blood IL-10 level, relative to the blood IL-10 level before administering IFNτ.

As used herein, the term "an IL-10 deficiency" refers generally to an amount of IL-10 in the body of a subject (i) that is at the lower end of the range of 'normal' IL-10 level, defined below, for the general population, or (ii) that is lower than what is considered a 'normal' IL-10 level for the general population. A 'normal' serum IL-10 level in the general population, taken as a population of healthy human subjects, is about 2.5-2200 pg/mL (Jankord, R. et al., *Medicine & Science in Sports & Exercise*, 36(6):960-964 (2004); Kozlowski, L. et al., *Annales Academiae Medicae Bialostocensis*, 48:82-84 (2003); Waubant et al., *J. Neuroimmunology*, 112:139-145 (2001)). Thus, an "IL-10 deficiency" in the blood (or serum) intends a level of IL-10 that is less than about 500 pg/mL, preferably less than 250 pg/mL, and still more preferably less than about 100 pg/mL. It will be appreciated that the amount of IL-10 can be determined by taking a sample of any suitable body fluid other than blood, such as spinal fluid or synovial fluid, from the subject and that an IL-10 deficiency would be determined based on the 'normal' range of IL-10 in that fluid for the general population. The level of IL-10 in a fluid sample is readily determined using, for example, a commercially available enzyme-linked immunosorbent assay (ELISA) kit.

It will be appreciated, and as evident from the normal range of blood IL-10 levels of 2.5-2200 pg/mL, that there is a natural variability in IL-10 levels. Thus, in one embodiment, a subject suspected of having an IL-10 deficiency can be identified by measuring the concentration of serum IL-10 in combination with an assessment of the subject's physical well-being. Assessment of the physical well-being can involve an inspection of the person for symptoms associated with conditions that are typically accompanied by a decreased IL-10 blood level, and exemplary conditions are given below. For example, persons with multiple sclerosis, active or in remission, typically have a decreased blood IL-10 level. A multiple sclerosis subject having an IL-10 blood level that is, for example, 600 pg/mL, may still be considered to have an "IL-10 deficiency" due to the combination of (i) the presence of a condition (multiple sclerosis), or symptoms associated with such a condition, typically accompanied by a decreased IL-10 blood level and (ii) a blood IL-10 level that is in the lower end of the 2.5-2200 pg/mL range of normal for the general population. The lower end of the normal range generally refers to the lower 30% of the range, for example less than about 700 pg/mL.

In one embodiment, a person having an IL-10 deficiency is identified by determining the IL-10 blood level, typically by obtaining a blood sample and analyzing the sample for IL-10 content. An IL-10 concentration that is less than about 500 pg/mL is indicative of an IL-10 deficiency and results in a positive identification of a subject with an IL-10 deficiency, even though the person may be asymptomatic for diseases or conditions associated with an IL-10 deficiency.

In another embodiment, a person having an IL-10 deficiency is identified by an IL-10 blood level that is within the 'normal' range but who is at risk of developing a condition that is induced or exacerbated by a decreased IL-10 concentration. For example, such persons may be those with a genetic predisposition to a condition caused, accompanied, or exacerbated by an IL-10 deficiency. Such persons may also be those who have been exposed to a causative agent, or at risk of exposure to a causative agent, that causes a condition typified by an IL-10 deficiency.

Persons identified as being IL-10 deficient, or at risk of being IL-10 deficient, are treated with IFNτ at a dose and for a period of time sufficient to achieve an increase in IL-10 concentration in vivo, as measured in a body fluid such as the blood. IFNτ is a type I IFN first identified as a pregnancy recognition hormone in ruminants, such as sheep and cows (Bazer, F. W. et al., *Am. J. Reprod. Immunol.* 26:19-22 (1991)). The protein possesses antiviral and anti-proliferative properties, with considerably lower toxicity than other type I interferons (Pontzer, C., et al., *Biochem. Biophys. Res. Comm.,* 152(2):801-807 (1988); Pontzer, C., et al., *Cancer Res.,* 51:5304 (1991)). Relative to other interferons, ovine IFNτ shares about 45-55% identity with IFN-αs from human, mouse, rat, and pig and 70% homology with bovine IFN-αII, now referred to as IFN-Ω. A cDNA of ovine IFNτ and several cDNA sequences which may represent different isoforms have been reported in the literature (Imakawa, K. et al, *Nature,* 330:377-379, (1987); Stewart, H. J., et al, *Mol. Endocrinol.* 2:65 (1989); Klemann, S. W., et al., *Nuc. Acids Res.* 18:6724 (1990); and Charlier, M., et al., *Mol. Cell Endocrinol.* 76:161-171 (1991)). All are approximately 1 kb with a 585 base open reading frame that codes for a 23 amino acid leader sequence and a 172 amino acid mature protein.

The 172 amino acid sequence of ovine-IFNτ is set forth, for example, in U.S. Pat. No. 5,958,402, and its homologous bovine-IFNτ sequence is described, for example, in Helmer et al., *J. Reprod. Fert.,* 79:83-91 (1987) and Imakawa, K. et al., *Mol. Endocrinol.,* 3:127 (1989). The sequences of ovine-IFNτ And bovine-IFNτ from these references are hereby incorporated by reference. An amino acid sequence of ovine IFNτ is shown herein as SEQ ID NO:1. A modified amino acid sequence of ovine IFNτ is shown herein as SEQ ID NO:2.

Recombinant production of IFNτ is described in both the scientific literature (Ott, et al., *J. Interferon Cytokine Res.,* 11:357-364 (1991); Soos, J. M. et al., *J. Immunol.,* 155:2747 (1995)) and the patent literature (WO/94/10313; U.S. 2003/0049277, the description of IFNτ production in these documents is incorporated by reference herein.)

As noted above, an amount of IFNτ is administered to the IL-10 deficient person at a dose and for a period of time effective to increase IL-10 level. Typically, a first dose of IFNτ is given to the subject for a first dosing period. After and/or during the first dosing period lapsed, the IL-10 level is measured to ascertain the person's response to the initial dose. If the IL-10 level is increased, the dose may remain the same for subsequent treatment, or can be adjusted if a further increase in IL-10 is desired, or if a less of an increase in IL-10 is desired, the dose can be decreased. In some cases, particularly where the original treatment dose is one sufficient to cause a desired IL-10 increase in most human patients, the dose may be decreased in an effort to minimize the dose yet maintain the desired IL-10 increase. If the IL-10 level has decreased or is unchanged after the initial dosing period, the IL-10 dose can be increased. However, if the initial dose of IFNτ was high and the patient does not respond by an increased IL-10 level, the attending caregiver may suggest an alternative approach which includes IFNτ in combination with an additional agent.

Thus, in some embodiments, the method of treating an IL-10 deficiency includes monitoring at one or more time points the IL-10 level in the subject during the first and/or subsequent treatment periods. The administered dose is refined based on the change in IL-10 level from the previous measurement or from the initial baseline (pretreatment) level.

After the first treatment period has lapsed and the subject is found to have an increased IL-10 level, treatment with IFNτ can continue indefinitely or for a period of time defined by the attending caregiver. Monitoring of the IL-10 level can be done as needed to determine when and if to discontinue treatment. Monitoring of the IL-10 level can also be done when treatment is discontinued to determine whether treatment should be resumed. For example, if the IL-10 level decreases upon cessation of treatment, then treatment can resume.

IFNτ can be provided to the subject in any pharmaceutically-acceptable vehicle or formulation and by any route of administration. Oral and parenteral modes of administration are preferred. Oral or parenteral preparations containing IFNτ can be formulated according to known methods for preparing pharmaceutical compositions.

In general, for oral administration IFNτ is formulated such that an effective amount of the IFNτ is combined with a suitable additive, carrier and/or excipient in order to facilitate effective oral administration of the composition. For example, tablets and capsules containing IFNτ may be prepared by combining IFNτ (e.g., lyophilized IFNτ protein) with additives such as pharmaceutically acceptable carriers (e.g., lactose, corn starch, microcrystalline cellulose, sucrose), binders (e.g., alpha-form starch, methylcellulose, carboxymethylcellulose, hydroxypropylcellulose, hydroxypropylmethylcellulose, polyvinylpyrrolidone), disintegrating agents (e.g., carboxymethylcellulose calcium, starch, low substituted hydroxy-propylcellulose), surfactants (e.g., Tween 80, polyoxyethylene-polyoxypropylene copolymer), antioxidants (e.g., L-cysteine, sodium sulfite, sodium ascorbate), lubricants (e.g., magnesium stearate, talc), or the like.

Further, IFNτ can be mixed with a solid, pulverulent or other carrier, for example lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets. By using several layers of the carrier or diluent, tablets that provide a slow or controlled release of IFNτ can be prepared.

Liquid preparations for oral administration can be made in the form of elixirs, syrups or suspensions, for example solutions containing from about 0.1% to about 30% by weight of IFNτ, amino acid or sugar and a mixture of ethanol, water, glycerol, propylene, glycol and possibly other additives of a conventional nature.

Another suitable formulation is a protective dosage form that protects the protein for survival in the stomach and intestines until absorbed by the intestinal mucosa. Protective dosage forms for proteins are known in the art, and include enteric coatings and/or mucoadhesive polymer coatings. Exemplary mucoadhesive polymer formulations include ethyl cellulose, hydroxypropylmethylcellulose, Eudragit®, carboxyvinly polymer, carbomer, and the like. A dosage form designed for administration to the stomach via ingestion for delivery of IFNτ in an active form to the intestinal tract, and particularly to the small intestine, is contemplated. Alternatively, IFNτ can be co-administered with protease inhibitors, stabilized with polymeric materials, or encapsulated in a lipid or polymer particle to offer some protection from the stomach and/or intestinal environment.

Selection of an appropriate dose of IFNτ for a given subject is well within the skill of an attending physician. It will be appreciated that proper dose varies from person to person based on the age and general state of health, and the extent of the IL-10 deficiency, and whether the person suffers from a condition typified by an IL-10 deficiency. As noted above, and as commonly done by physicians, selection of the dose may involve "dose-titrating" the subject; that is, to start the subject on a dosing regimen which is at a level or just below a level required to produce the desired IL-10 increase, and gradually increase the dose until the desired increase is achieved. The dose of IFNτ when for oral treatment is typically in the range of greater than about $1 \times 10^5$ Units per day, and preferably greater than about $5 \times 10^8$ Units per day and up to about $10^{12}$ Units per day; more specifically, the dose is greater than about $5 \times 10^8$ Units per day, more preferably about $0.5 \times 10^9$ Units or more per day, still more preferably about $1 \times 10^9$ Units or more per day. The expected specific activity of IFNτ is between $1 \times 10^8$ Units/mg and $1 \times 10^8$ Units/mg. The dose can be adjusted to achieve a desired initial increase in blood IL-10, e.g., between 1.5 and 4 fold of the IL-10 level prior to initiation of treatment.

It will be appreciated that the method may also include monitoring the change in IL-10 level in the subject being treated to ascertain whether the level is modulated, for example, whether the level is increased relative to the IL-10 level prior to treatment. Monitoring can also be done to determine whether or not an adjustment in the dose is desirable. Such monitoring can be done on a periodic basis at one or more time points during initial treatment. The information gathered from the monitoring can be used to determine how long to continue treatment, whether to adjust the dose to achieve a desired IL-10 response, and the like.

A study was done to illustrate treatment of a subject having an IL-10 deficiency with IFNτ. As described in Example 1, person having an IL-10 deficiency was identified by measuring an IL-10 blood concentration of 5.8 pg/mL. The patient also suffered from multiple sclerosis. The subject was treated with IFNτ (SEQ ID NO:2) administered at a dose of 1.8 mg per day ($1.8 \times 10^8$ U/day) orally for 29 days. Serum IL-10 concentration was monitored during the dosing period and after cessation of treatment. The serum IL-10 level is shown in FIG. 1.

FIG. 1 shows the IL-10 concentration as a function of time during the 28 day treatment period. The IL-10 concentration increased over the 28 day dosing period. The extent of the increase can be determined, for example, by a simple percent increase or by comparing the area-under-the-curve (AUC) for serum IL-10 levels over an initial treatment period to the level of serum IL-10 that would be expected over the same period in the absence of any treatment, i.e., a baseline IL-10 level. FIG. 1 illustrates the AUC comparison for the subject, where the AUC for the IL-10 increase is the total area under the curve defined by the IL-10 measurements in the treated subject. The baseline value may be calculated as the area under the curve defined by an initial value taken at the time treatment is initiated (or before initiation of treatment) and is considered over the same time period of Day 1 to Day 28, and calculated as the area of the resulting rectangle. Alternatively, the baseline value may be calculated as a true area under the curve by taking a number of IL-10 measurements prior to treatment and calculating an AUC value for the baseline value. In the latter case, the baseline AUC and IL-10 AUC have to be corrected to the same sampling period, e.g., 28 days, before taking the ratio of the two AUC's.

The AUC may be calculated easily using the Trapezoidal Rule, in which the area to be measured is broken up into multiple trapezoids and the sum of the area of all of the trapezoids is determined and represents the area under the curve. In performing these calculations an area under the curve for the post-treatment points in FIG. 1 was obtained (all area under the curve values are in units of pg days/mL.) The baseline AUC was calculated, as above, simply as the area of the baseline rectangle shown. A ratio of the AUC after treatment to the AUC prior to treatment that is greater than 1 indicates a positive increase in IL-10 concentration. The subject in Example 1 had an AUC ratio of 1.87.

Figure 2:
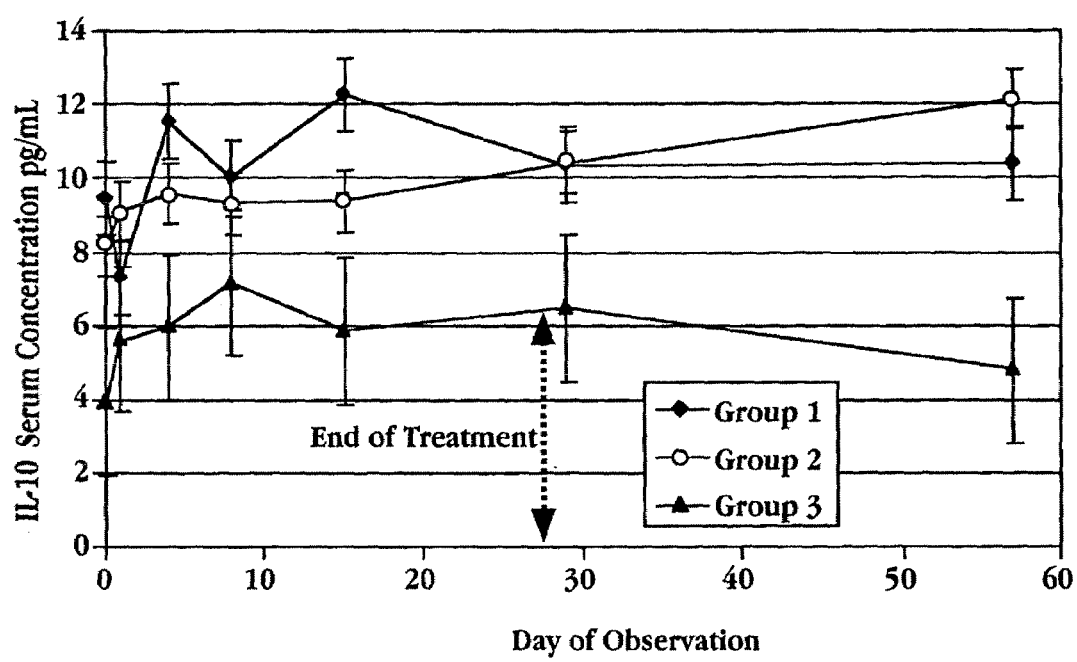
FIG. 2 is a plot of IL-10 serum concentration as a function of time, in days, for three groups of five patients each treated with varying doses of IFNτ; Group I, 0.2 mg IFNτ (diamonds), Group II, 0.6 mg IFNτ (circles), and Group III, 1.8 mg IFNτ (triangles) from days 1-28.

A study was conducted on persons having an IL-10 deficiency and afflicted with multiple sclerosis, as described in Example 2. Three groups of five patients each were each given a selected daily dose of 0.2 (Group I; $2 \times 10^7$ U), 0.6 (Group II; $6 \times 10^7$ U), and 1.8 mg (Group III; $1.8 \times 10^8$ U), over a 28 day initial treatment period. Serum IL-10 was monitored at Days, 1, 4, 8, 15, and 29, and the average serum level for each group is shown in FIG. 2.

The IL-10 increase of each patient was determined by an area-under the curve calculation described in Example 1, with the results shown in Table 1.

TABLE 1

| Increase in IL-10 IL-10 response in MS patients at three different doses | | | |
|---|---|---|---|
| Group No. and Patient No. | AUC ratio (0.2 mg) | AUC ratio (0.6 mg) | AUC ratio (1.8 mg) |
| I-1, II-1, III-1 | 1.04 | 1.26 | 1.67 |
| I-2, II-2, III-2 | 0.99 | 1.08 | 1.87 |
| I-3, II-3, III-3 | 0.96 | 0.99 | 1.85 |
| I-4, II-4, III-4 | 1.74 | 0.86 | 2.37 |
| I-5, II-5, III-5 | 1.28 | 1.86 | 0.97 |

From this table, it can be seen that, first, the highest IL-10 responses are in the range of about 1.5 and higher, that is about 50% higher than baseline. These responses are seen at the highest dose in four of the five patients and in one patient each at the lower two doses, indicating that the highest dose of 1.8 mg daily is a good starting dose for the initial treatment period. Reducing the dose from this level would not be expected to enhance the IL-10 response, and if a patient receiving an initial 1.8 mg/daily dose does not show an IL-10 increase of at least about 1.5, the dose should be increased, not decreased in an effort to boost the IL-10 response.

Figure 3:
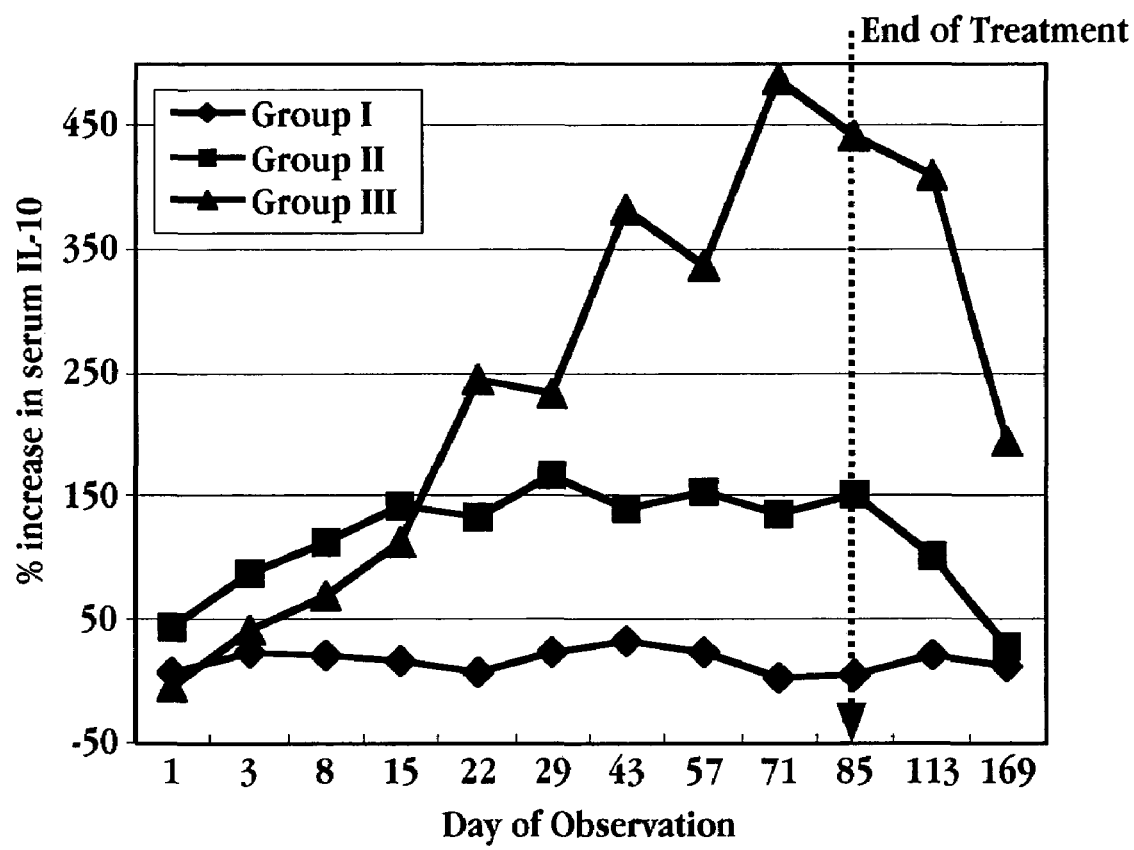
FIG. 3 plot of percent increase in serum IL-10 concentration as a function of time, for the three test groups of patients having an IL-10 deficiency and a hepatitis C viral infection, where six patients in Test Group I were treated daily with 0.33 mg IFNτ three times daily (diamonds), six patients in Test Group II were treated daily with 1.0 mg IFNτ three times daily (squares); and six patients in Test Group IIII were treated daily with 3 mg IFNτ three times daily (triangles).

In another study, detailed in Example 3, patients with an IL-10 deficiency and suffering from hepatitis C were divided into three groups for treatment with daily doses of IFNτ of 1 mg (Group I), 3 mg (Group II), and 9 mg (Group II) daily, where the doses were administered three time daily, i.e., at individual doses of 0.33, 1, and 3 mg, and over an 84 day period. Serum IL-10 levels were monitored at Days 1, 3, 8, 15, 22, 29, 43, 71, and 85. The IL-10 concentrations of the patients in each treatment group were averaged, and the results are shown in FIG. 3. FIG. 3 shows the percent increase in serum IL-10 concentration as a function of time, for the three test groups of patients having an IL-10 deficiency. The average percent increase in serum IL-10 levels in the subjects treated with a daily dose of 1 mg ($1 \times 10^8$ Units/day; diamonds) was less than about 40% over the treatment period. Groups II and III, treated with higher doses of IFNτ of 3 mg ($3 \times 10^8$ Units/day; squares) and 9 mg ($9 \times 10^8$ Units/day; triangles) was considerably higher, with an increase of more than 50% over the majority of the treatment period. Thus, in one embodiment, the method of treating an IL-deficiency involves administering IFNτ at a dose sufficient to increase serum IL-10 by at least about 50% four days after an initial dose, and more preferably by at least about 100% after two weeks of treatment.

Conditions in which a relative deficiency of IL-10 has pathophysiological relevance include, but are not limited to, psoriasis, acne, allergic contact dermatitis and other non-atopic eczemas, chronic inflammatory bowel diseases, arthritis, multiple sclerosis, transplantation, uveitis, aging, allergic asthma, and Chron's disease. Without intending to be limited, several of these conditions will be further discussed, and the results of studies on patients with an IL-10 deficiency and a particular condition will be described.

1. Psoriasis

There are two main types of psoriasis: psoriasis vulgaris (plaque psoriasis) and psoriasis pustulosa (pustular psoriasis). The different types of psoriasis can be divided into subgroups according to severity, duration, location on the body and appearance of the lesions. The severity of skin lesions can be assessed using a variety of scoring tests described in the literature, for example the Physician's Static Global Assessment score, a scaling score, a plaque score, or an erythema score. Cutaneous IL-10 mRNA expression in psoriasis lesions is typically lower than the IL-10 mRNA expression in healthy skin, indicating a relative IL-10 deficiency in psoriatic lesions (Asadullah, K., et al., *Pharmacol Rev* 55(2):241-69 (2003)). Additionally, the IL-10 level in the blister fluid of lesions associated with psoriasis also indicates an IL-10 deficiency (Nickoloff, B. J., et al., *Clin. Immunol. Immunopathol.*, 73:63-68 (1994)).

Accordingly, to treat the IL-10 deficiency in persons afflicted with psoriasis, the subject is treated with IFNτ until the IL-10 level increases sufficiently to result in a reduction of the psoriatic lesions, as assessed in a clinically suitable scoring test. Preferably the reduction in the assessment score is of at least about 50%, more preferably at least about 70%, still more preferably of at least about 80%. By way of example, a person having psoriasis is treated with an initial dose of IFNτ, typically an oral dose of greater than about $5 \times 10^8$ Units/day. Prior to treatment, a blood sample can be taken or the skin lesions can be analyzed for IL-10 concentration. The dose is given for a first dosing period, of for example, 3-4 weeks. After and or during the first dosing period, the subject is monitored for IL-10 level and/or for reduction in skin lesions. The dose can be adjusted as needed to effect the desired increase in IL-10 in order to achieved the desired reduction in lesions.

2. Allergic Contact Dermatitis

Allergic contact dermatitis is a type 1 cytokine-dominated immune reaction, with accompanying decreased levels of the type 2 cytokine IL-10 (Asadullah, K., et al., *Pharmacol Rev* 55(2):241-69 (2003)). Application if IL-10 epicutaneously has been shown to block the effector phase in allergic contact hypersensitivity reactions (Schwarz, A. et al., *J. Invest. Dermatol*, 103:211-216 (1994)), suggesting that a treatment method that can normalize the IL-10 deficiency that accompanies allergic contact dermatitis would be beneficial. Accordingly, an IL-10 deficient person suffering from allergic contact dermatitis is treated with IFNτ at a dose sufficient to increase the IL-10 blood level, thus alleviating the condition or the symptoms associated with the condition.

3. Chronic Inflammatory Bowel Disease

An IL-10 deficiency has been shown to result in the development of inflammatory bowel disease. Specifically, mice deficient in IL-10 production, so-called IL-10 knock-out mice, develop severe inflammatory bowel disease and death by uncontrolled inflammation (Kuhn, R. et. al., *Cell*, 75:263-274 (1993); Lindsay, J. O. et al., *Immunol. Rev.*, 184:117-128 (2001)). Inflammatory bowel disease refers to a group of gastrointestinal disorders characterized by chronic non-specific inflammation of portions of the gastrointestinal tract. Ulcertative colitis and Crohn's Disease are prominent examples of inflammatory bowel disease in humans. Administration of IFNτ to persons diagnosed with an inflammatory bowel disease or at risk of developing an inflammatory bowel disease due, for example, to a genetic predisposition, can be treated with IFNτ at a dose sufficient to increase the blood IL-10 level, thus alleviating the condition or the symptoms associated with the condition or minimizing the risk of developing the condition.

4. General Treatment of Inflammatory Disorders

Inflammatory bowel disease, acne and dermatitis are examples of inflammatory disorders, illustrative of the more general method of treating an IL-10 deficiency associated with inflammatory disorders in general. IL-10 controls inflammatory processes by suppressing the expression of proinflammatory cytokines, chemokines, adhesion molecules, as well as antigen-presenting and costimulatory molecules in monocytes/macrophages, neutrophils, and T cells. IL-10 blocks nuclear translocation of classic NF-kB. Thus, administration of IFNτ to persons suffering from an inflammatory disorder at a dose sufficient to increase the blood IL-10 level will alleviate the condition or the symptoms associated with the condition.

5. Treatment of Immunosenescence

IL-10 also appears to play a role in age-related decline in physical functions associated with immunosenescence. Deficient IL-10 levels have been found in frail elderly persons, relative to the IL-10 levels in healthy elderly persons (Uyemura, K. et al., *Mech. Ageing Dev.*, 123:955-962 (2002)). The presence of anti-inflammatory cytokines is believed to be involved in successful aging and longevity. Thus, administration of IFNτ to elderly persons at a dose sufficient to increase the blood IL-10 level will alleviate any conditions of fragility due to aging.

6. Combination Treatment

IL-10 activity is mediated by its specific cell surface receptor complex, which is expressed on a variety of cells, in particular immune cells. A few copies of the IL-10 receptor complex are expressed on the surface of such cells, however the expression is variable and can be stimulated by various agents. For example, endotoxin increases the expression of IL-10 receptor complex on fibroblasts (Weber-Nordt, R. M. et al., *J. Immunol.*, 153:3734-3744 (1994)) and dermatological therapeutic agents such as glucocorticoids, vitamin D3, and calcipotriol increase expression of the receptor (Michel, G. et al., *Inflamm Res.*, 46:32-34 (1997)).

Accordingly, in one embodiment, administration of IFNτ in combination with an agent that increases the expression of the IL-10 cell surface receptor complex is provided. The second agent can be administered by any suitable route, particularly including oral and topical. The second agent can be administered prior to, during, and/or concurrent with delivery of INF-τ.

In another embodiment, administration of IFNτ in combination with a second therapeutic agent is contemplated. IFNτ is provided to correct the decreased IL-10 blood level and a second agent may be provided to treat symptoms or to treat an underlying basis for the decreased IL-10, such as any of the diseases or conditions described above.

It will be appreciated that IFNτ can be administered to persons having an IL-10 deficiency with no accompanying disease or condition, or to persons having a condition that results in an IL-10 deficiency, or to persons having a condition that is exacerbated by an IL-10 deficiency, or to persons at risk of developing a condition that is caused by or exacerbated by an IL-10 deficiency. In some cases, IFNτ is administered prior to positive identification of an IL-10 deficiency by a blood test, but is administered to a person suspected of having an IL-10 deficiency based on outward visual symptoms.

III. EXAMPLES

Reference will now be made to specific examples illustrating the invention described above. It is to be understood that the examples are provided to illustrate preferred embodiments and that no limitation to the scope of the invention is intended thereby.

Example 1

Administration of IFNτ to IL-10 Deficient Subject

Blood samples from a person suffering from multiple sclerosis were drawn on two different days. The samples were analyzed for IL-10 concentration using a commercially available ELISA kit (Genzyme, Cambridge, Mass.). The average IL-10 concentration in the samples was 5.9 pg/mL, indicating that the subject was IL-10 deficient. The subject was treated with IFNτ, synthetically produced as described in U.S. 2003/0049277 and having a specific activity of about $1 \times 10^8$ antiviral U/mg protein and $1 \times 10^9$ antiviral U/mg protein, assessed using a standard cytopathic effect assay (Familletti, P. C., et al., *Methods in Enzymology*, 78:387-394 (1981); Rubinstein, S. et al., *J. Virol*, 37:755-758 (1981)).

The person was treated with IFNτ orally at a dosage of 1.8 mg per day ($1.8 \times 10^8$ U/day) for 28 days. Prior to administration, the vials of IFNτ (SEQ ID NO:2) and syringes were kept in a refrigerator maintained at 2 to 8° C. Prior to self-administration of medication, the patient removed one vial and one syringe from the refrigerator. The cap was removed from the tip of the syringe and the tip of the syringe was placed into the bottle of medication to withdraw the appropriate volume into the syringe. The tip of the syringe was placed in the mouth and the syringe contents were emptied into the mouth by depressing the plunger. The patient then swallowed, and if desired, was allowed to drink a glass of water. The patient noted the date and time the dose was administered. Blood samples were taken during the dosing period on days 1, 4, 8, 15 and 29, and again on day 57, after cessation of treatment. The samples were analyzed for IL-10 concentration using commercially available ELISA kits. The results are shown in FIG. 1.

Example 2

Treatment of IL-10 Deficiency in Subjects

The human patients in this study had an IL-10 deficiency, which is common in multiple sclerosis. Fifteen patients were randomized into three treatment groups, summarized in the table, for treatment with a once daily dose of IFNτ orally.

|  | Group I (n = 5) | Group II (n = 5) | Group III (n = 5) |
|---|---|---|---|
| IFNτ Oral Dose[1] | 0.2 mg/day ($2 \times 10^7$ U) | 0.6 mg/day ($6 \times 10^7$ U) | 1.8 mg/day ($1.8 \times 10^8$ U) |
| Average Weight | 67.2 kg | 58.9 kg | 90.0 kg |
| Average Age | 39 | 34.5 | 47 |

[1] 1 mg IFNτ = $1 \times 10^8$ Units

Prior to treatment with IFNτ, on screening Day and Day 1 (one), a blood sample was taken from each subject to determine a baseline serum cytokine concentration. Treatment was initiated by administering IFNτ orally to each patient following the blood draw on Day 1. Prior to administration, the vials of IFNτ (SEQ ID NO:2) and syringes were kept in a refrigerator maintained at 2 to 8° C. Prior to self-administration of medication, the patient removed one vial and one syringe from the refrigerator. The cap was removed from the tip of the syringe and the tip of the syringe was placed into the bottle of medication to withdraw the appropriate volume into the syringe as instructed at the clinic on Day 1. The tip of the syringe was placed in the mouth and the syringe contents were emptied into the mouth by depressing the plunger. The patient then swallowed, and if desired, was allowed to drink a glass of water. The patient noted on his/her diary card the date and time the dose was administered.

Blood samples were taken from each patient on Days 1, 4, 8, 15, 29, and 57 of the study. The samples were analyzed for IL-10 concentrations by using commercially available ELISA kits (Genzyme, Cambridge, Mass.). The AUC ratio of IL-10 concentration versus time after treatment to before treatment was determined as described in Example 1, with the results shown in Table 1. The average increase in serum IL-10 concentration for each group was determined as is shown in FIG. 2.

Example 3

Treatment of IL-10 Deficiency in Subjects Infected with Hepatitis C

Eighteen patients afflicted with hepatitis C and having decreased IL-10 blood levels were randomized into three treatment groups for treatment with IFNτ.

| Dose Group | Number of Patients | IFNτ (mg/mL) | Volume (mL) per Dose (TID) | Total Daily Dose (mg) | Total Daily Dose (U) |
|---|---|---|---|---|---|
| I | 6 | 1.0 | 0.33 | 1.0 | $1 \times 10^8$ |
| II | 6 | 1.0 | 1.0 | 3.0 | $3 \times 10^8$ |
| III | 6 | 1.0 | 3.0 | 9.0 | $9 \times 10^8$ |

The IFNτ was administered to the subjects as described in Example 2, except the prescribed dose was taken three times per day at approximately eight-hour intervals: once in the morning, once at midday, and once in the evening. The treatment period was 84 days for each patient.

Blood samples were taken at defined intervals over a 169 day test period. The samples were analyzed for IL-10 levels in the serum using ELISA kits (Genzyme, Cambridge, Mass.) following the manufacturer's instructions. The IL-10 blood concentration of the six subjects in each group were averaged and the percent increase relative to each group's average baseline, pretreatment IL-10 blood level, is shown in FIG. 3.

A statistical analysis found a statistical significant difference between the three groups (F=12.08, P=0.0009), a significant effect of time (F=11.20, P=0.0001) and a significant group-by-time interaction (F=7.88, P=0.001). The latter finding is clearly seen by the difference in IL-10 response rates between the three dose groups over time. While the lowest dose group (Group I; 0.33 mg TID) produced a 22% increase in IL-10 levels from Day 1 to Day 43, Group II (1 mg TID) produced a peak response of 114% by Day 29. In contrast, Group III (3 mg TID) produced a 387% increase by Day 43 with a peak of 484% by Day 71.

Although the invention has been described with respect to particular embodiments, it will be apparent to those skilled in the art that various changes and modifications can be made without departing from the invention.

It is claimed:

1. A method for increasing IL-10 levels in a patient with multiple sclerosis comprising identifying a human subject afflicted with multiple sclerosis; and administering an interferon-tau having greater than about 90% sequence identity to SEQ ID NO:1 in an amount effective to increase blood IL-10 level relative to the blood IL-10 level before administering interferon-tau.

2. The method of claim 1, wherein said identifying comprises obtaining a blood sample from the subject and analyzing the sample for IL-10 concentration.

3. The method of claim 2, wherein said administering includes administering to a subject who is asymptomatic for multiple sclerosis.

4. The method of claim 3, wherein said administering comprises administering interferon-tau at a first dose for a first period of time of about one month or less, determining the blood IL-10 concentration after said first period of time, and administering a second dose for a second period of time, of about one month or less.

5. The method of claim 4, wherein said second dose is less than said first dose.

6. The method of claim 4, wherein said second dose is greater than said first dose.

7. The method of claim 1, wherein said administering includes administering interferon-tau orally.

8. The method of claim 7, wherein said administering includes administering interferon-tau orally at a daily dosage of greater than $5 \times 10^8$ Units.

9. The method of claim 1, further comprising monitoring the IL-10 level by obtaining a blood sample from the subject and analyzing the sample for IL-10 concentration.

* * * * *